(12) United States Patent
Foster et al.

(10) Patent No.: US 8,346,374 B2
(45) Date of Patent: Jan. 1, 2013

(54) LAMINATE DISTAL LEAD SEAL WITH TISSUE INGROWTH FEATURE

(75) Inventors: Daniel J. Foster, Lino Lakes, MN (US); Arthur J. Foster, Centerville, MN (US); Duane T. Meyer, St. Paul, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 328 days.

(21) Appl. No.: 12/818,696

(22) Filed: Jun. 18, 2010

(65) Prior Publication Data

US 2011/0009939 A1  Jan. 13, 2011

Related U.S. Application Data

(60) Provisional application No. 61/224,086, filed on Jul. 9, 2009.

(51) Int. Cl.
*A61N 1/05* (2006.01)
(52) U.S. Cl. .................................................. 607/127
(58) Field of Classification Search .................. None
See application file for complete search history.

(56) References Cited

U.S. PATENT DOCUMENTS

| 4,311,153 | A | | 1/1982 | Smits |
| 4,628,943 | A | * | 12/1986 | Miller ............................ 607/127 |
| 5,824,030 | A | * | 10/1998 | Yang et al. .................... 607/122 |
| 6,097,986 | A | | 8/2000 | Janke et al. |
| 7,082,336 | B2 | | 7/2006 | Ransbury et al. |
| 7,112,293 | B2 | | 9/2006 | Dubson et al. |
| 7,115,220 | B2 | | 10/2006 | Dubson et al. |
| 7,197,362 | B2 | * | 3/2007 | Westlund ....................... 607/127 |
| 7,657,324 | B2 | | 2/2010 | Westlund et al. |
| 2008/0161871 | A1 | * | 7/2008 | Knapp et al. ...................... 607/5 |

* cited by examiner

*Primary Examiner* — Carl H Layno
*Assistant Examiner* — Paula J Stice
(74) *Attorney, Agent, or Firm* — Faegre Baker Daniels LLP (57) ABSTRACT

An implantable lead may include a housing and a laminate distal seal disposed across a distal end of the housing. A coupler and a fixation helix secured to the coupler may be disposed within the housing. The fixation helix may have a retracted position in which the fixation helix does not penetrate the laminate distal seal and an extended position in which the fixation helix has pierced the laminate distal seal and extends therethrough.

6 Claims, 6 Drawing Sheets

LAMINATE DISTAL LEAD SEAL WITH TISSUE INGROWTH FEATURE

CROSS-REFERENCE TO RELATED APPLICATIONS

This application claims the benefit under 35 U.S.C. §119 (e) to U.S. Provisional Patent Application No. 61/224,086, filed on Jul. 9, 2009, entitled "Laminate Distal Lead Seal with Tissue Ingrowth Feature," which is incorporated herein by reference in its entirety.

TECHNICAL FIELD

The present invention relates to implantable medical devices and relates more particularly to leads for cardiac rhythm management (CRM) systems.

BACKGROUND

Various types of medical electrical leads for use in cardiac rhythm management (CRM) and neurostimulation systems are known. For CRM systems, such leads are typically extended intravascularly to an implantation location within or on a patient's heart, and thereafter coupled to a pulse generator or other implantable device for sensing cardiac electrical activity, delivering therapeutic stimuli, and the like. The leads frequently include features to facilitate securing the lead to heart tissue to maintain the lead at its desired implantation site.

SUMMARY

Example 1 is an implantable lead having a flexible body extending between a proximal end and a distal end. A connector assembly including a terminal pin rotatable relative to the body is secured to the proximal end for coupling the lead to an implantable medical device. A conductor member that is rotatable relative to the body is disposed longitudinally within the body and is coupled to the terminal pin. The lead has a distal assembly that is coupled to the distal end of the body and that includes a housing having a distal region and a proximal region, the proximal region fixedly coupled to the distal end of the body, the distal region including a distal end. A coupler is rotatably disposed within the housing, the coupler having a proximal end and a distal end, the proximal end connected to the conductor member. A helical electrode is fixedly secured to the coupler and a laminate distal seal is disposed across the distal end of the housing and at least substantially seals an interior of the housing. The laminate distal seal includes an inner ePTFE layer, an outer ePTFE layer and an intervening elastomeric layer. The terminal pin is rotatably engaged with the coupler via the conductor member such that rotation of the terminal pin causes the coupler and the helical electrode to rotate and therefore translate relative to the housing.

In Example 2, the implantable lead of Example 1 in which the helical electrode pierces the laminate distal seal as the helical electrode translates distally.

In Example 3, the implantable lead of Example 1 or Example 2 in which the inner ePTFE layer and the outer ePTFE layer each have a predominant grain direction, the inner ePTFE layer and the outer ePTFE layer disposed so that the predominant grain direction of each of the two layers are offset from each other.

In Example 4, the implantable lead of any of Examples 1-3 in which the elastomeric layer includes silicone.

In Example 5, the implantable lead of any of Examples 1-4 in which the inner ePTFE layer is configured to be easily penetrated by the helical electrode to help guide the helical electrode into the laminate distal seal.

In Example 6, the implantable lead of any of Examples 1-5 in which the outer ePTFE layer is configured to inhibit tissue ingrowth.

In Example 7, the implantable lead of any of Examples 1-5 in which the outer ePTFE layer is configured to encourage tissue ingrowth.

Example 8 is a lead that is configured to carry an electrical signal. The lead includes a flexible body that extends between a proximal end and a distal end and that is configured to carry an electrical signal from the proximal end to the distal end. A distal assembly is coupled to the distal end of the body and includes a housing having a distal region and a proximal region, the proximal region fixedly coupled to the distal end of the body, the distal region including a distal end. A coupler is rotatably disposed within the housing, the coupler having a proximal end and a distal end, the proximal end connected to the conductor member. The lead includes a laminate distal seal that at least substantially seals an interior of the housing and that is stretched across the distal end of the housing, the laminate distal seal including an elastomeric layer and at least one expanded polytetrafluoroethylene layer. A fixation helix is fixedly secured to the coupler and has a retracted position in which the fixation helix does not extend into or through the laminate distal seal and an extended position in which the fixation helix extends through the laminate distal seal.

In Example 9, the implantable lead of Example 8 in which the elastomeric layer at least partially seals around the fixation helix when the fixation helix penetrates the laminate distal seal.

In Example 10, the implantable lead of either Example 8 or Example 9 in which the at least one expanded polytetrafluoroethylene layer faces the fixation helix and has an average pore size that enables the fixation helix to drive into and through the expanded polytetrafluoroethylene layer.

In Example 11, the implantable lead of any of Examples 8-10 in which the elastomeric layer includes silicone.

In Example 12, the implantable lead of any of Examples 8-11, further including a fixation ring disposed about the distal region of the housing, the fixation ring at least partially holding the laminate distal seal in position.

In Example 13, the implantable lead of Example 12 in which the fixation ring is a metal ring and is sized to provide a compressive fit about the distal region of the housing and a periphery of the laminate distal seal to secure the laminate distal seal in position.

In Example 14, the implantable lead of Example 12 in which the fixation ring is a polymer ring and is configured to be at least partially melted to secure the laminate distal seal in position.

In Example 15, the implantable lead of any of Examples 8-14 in which the laminate distal seal is disposed approximately perpendicular to a longitudinal axis of the housing.

Example 16 is an implantable lead that is configured to carry an electrical signal. The lead includes a flexible body that extends between a proximal end and a distal end and that is configured to carry an electrical signal from the proximal end to the distal end. A distal assembly is coupled to the distal end of the body and includes a housing having a distal region and a proximal region, the proximal region fixedly coupled to the distal end of the body, the distal region including a distal end. The lead includes a fixation helix extending distally from the housing and a laminate distal seal including an elastomeric layer and at least one ePTFE layer is disposed across the distal end of the housing and at least substantially seals an interior of the housing. The fixation helix extends through the laminate distal seal, the laminate distal seal sealing around the fixation helix to prevent fluid inflow into the housing.

In Example 17, the implantable lead of Example 16 in which the at least one ePTFE layer is disposed on an exterior side of the elastomeric layer.

In Example 18, the lead of Example 16 or Example 17 in which the at least one ePTFE layer is configured to encourage tissue growth.

In Example 19, the implantable lead of any of Examples 16-18 in which the fixation helix is moveable relative to the housing.

In Example 20, the implantable lead of any of Examples 16-18 in which the fixation helix is stationary relative to the housing.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
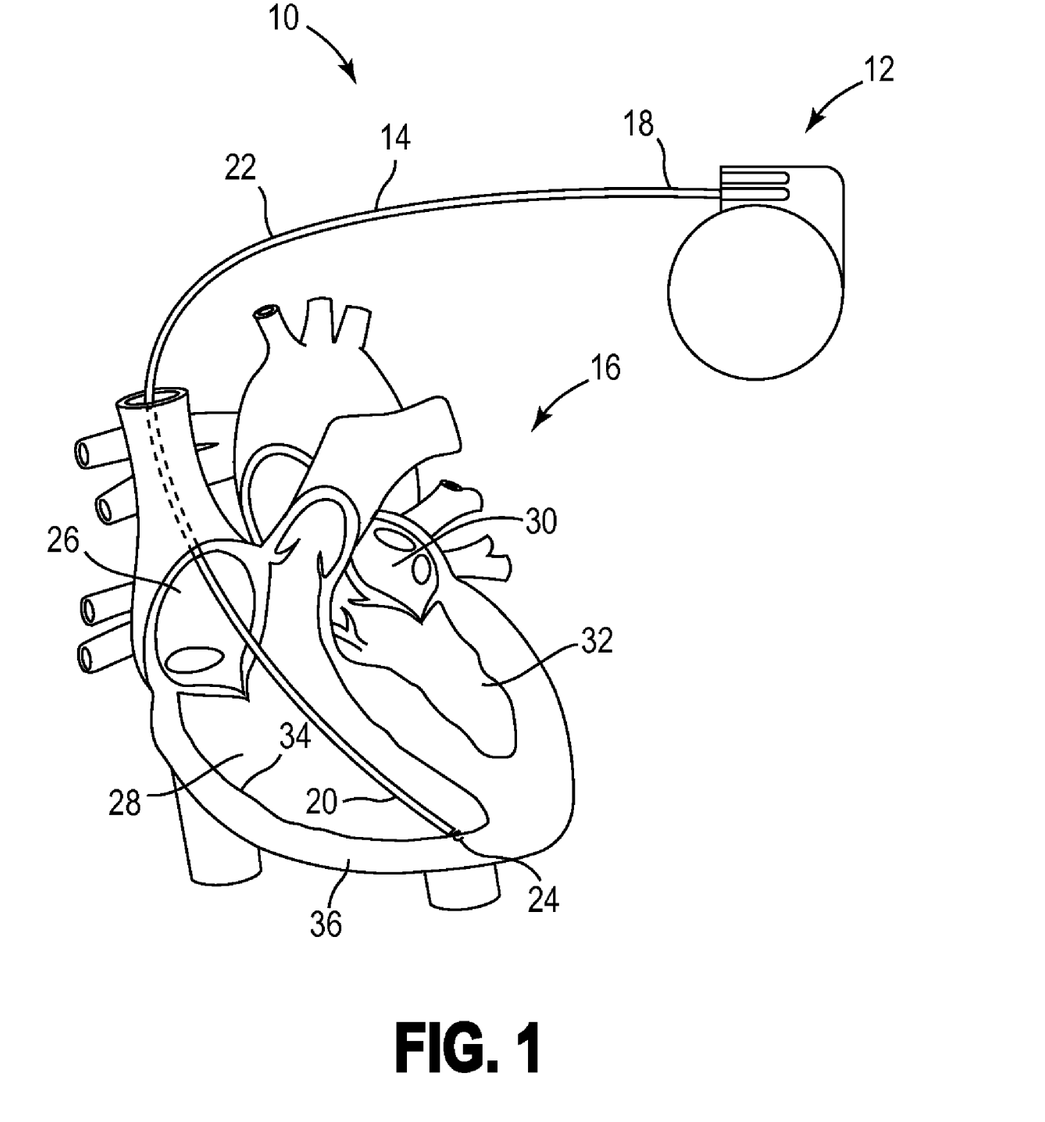
FIG. 1 is a combined cutaway and perspective view of an implantable medical device and lead in accordance with an embodiment of the present invention.

FIG. 1 is a perspective view of an implantable cardiac rhythm management (CRM) system 10. The CRM system 10 includes a pulse generator 12 and a cardiac lead 14. The lead 14 operates to convey electrical signals between the heart 16 and the pulse generator 12. The lead 14 has a proximal region 18 and a distal region 20. The lead 14 includes a lead body 22 extending from the proximal region 18 to the distal region 20. The proximal region 18 is coupled to the pulse generator 12 and the distal region 20 is coupled to the heart 16. The distal region 20 includes a fixation helix 24, which as will be discussed in greater detail below, locates and/or secures the distal region 20 within the heart 16.

As will be explained in detail below, the lead 14 includes a multilayer or laminate distal seal that prevents or at least substantially prevents fluid inflow into an interior of the lead 14. In some embodiments, the distal seal includes an outer layer that encourages tissue ingrowth. In some embodiments, the distal seal includes an outer layer that discourages tissue ingrowth. In some embodiments, the distal seal includes an inner layer that is configured to facilitate penetration of the distal seal by the fixation helix 24. It is contemplated that the laminate distal seal may simplify the construction of the lead 14 by reducing or eliminating a need for seals that might otherwise be disposed internally within the lead 14.

The pulse generator 12 is typically implanted subcutaneously within an implantation location or pocket in the patient's chest or abdomen. The pulse generator 12 may be any implantable medical device known in the art or later developed, for delivering an electrical therapeutic stimulus to the patient. In various embodiments, the pulse generator 12 is a pacemaker, an implantable cardioverter/defibrillator (ICD), a cardiac resynchronization (CRT) device configured for bi-ventricular pacing, and/or includes combinations of pacing, CRT, and defibrillation capabilities.

The lead body 22 can be made from any flexible, biocompatible materials suitable for lead construction. In various embodiments, the lead body 22 is made from a flexible, electrically insulative material. In one embodiment, the lead body 22 is made from silicone rubber. In another embodiment, the lead body 22 is made from polyurethane. In various embodiments, respective segments of the lead body 22 are made from different materials, so as to tailor the lead body characteristics to its intended clinical and operating environments. In various embodiments, the proximal and distal ends of the lead body 22 are made from different materials selected to provide desired functionalities.

As is known in the art, the heart 16 includes a right atrium 26, a right ventricle 28, a left atrium 30 and a left ventricle 32. It can be seen that the heart 16 includes an endothelial inner lining or endocardium 34 covering the myocardium 36. In some embodiments, as illustrated, the fixation helix 24, located at the distal region 20 of the lead, penetrates through the endocardium 34 and is imbedded within the myocardium 36. In one embodiment, the CRM system 10 includes a plurality of leads 14. For example, it may include a first lead 14 adapted to convey electrical signals between the pulse generator 12 and the right ventricle 28 and a second lead (not shown) adapted to convey electrical signals between the pulse generator 12 and the right atrium 26.

In the illustrated embodiment shown in FIG. 1, the fixation helix 24 penetrates the endocardium 34 of the right ventricle 28 and is embedded in the myocardium 36 of the heart 16. In some embodiments, the fixation helix 24 is electrically active and thus can be used to sense the electrical activity of the heart 16 or to apply a stimulating pulse to the right ventricle 28. In other embodiments, the fixation helix 24 is not electrically active. Rather, in some embodiments, other components of the lead 14 are electrically active.

Figure 2:
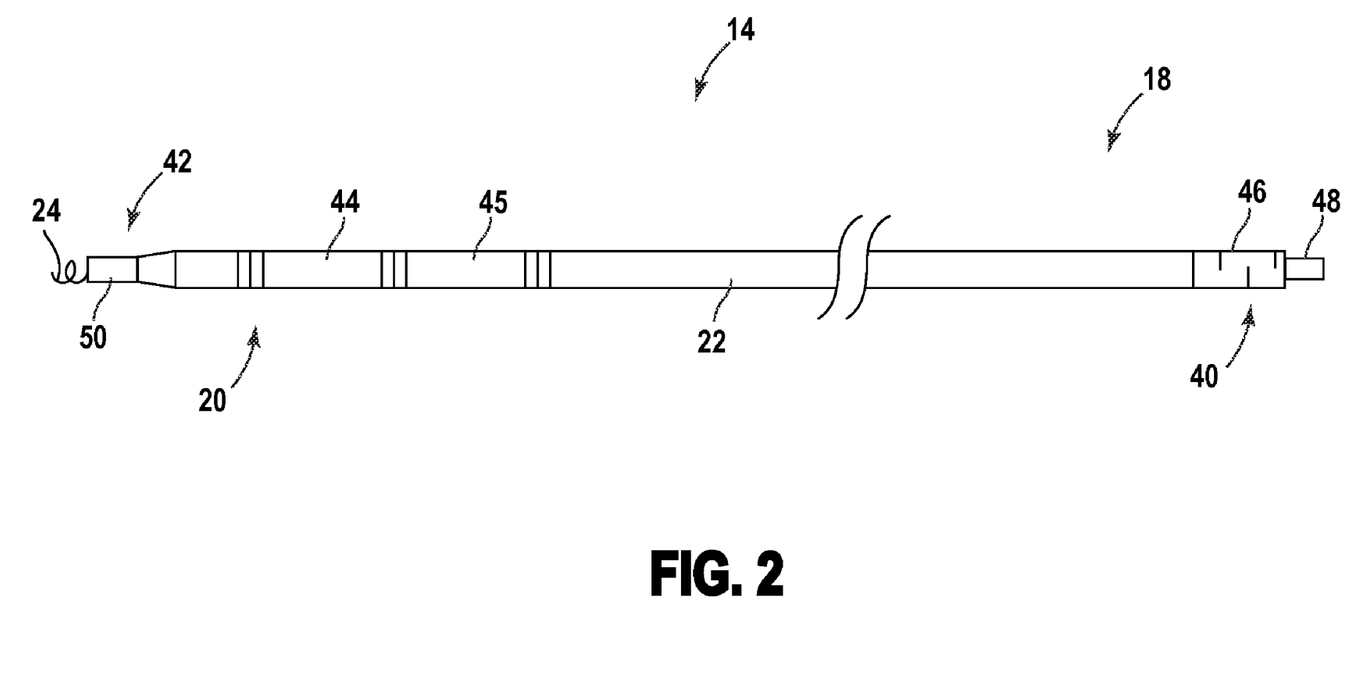
FIG. 2 is a side elevation view of the lead of FIG. 1.

FIG. 2 is an isometric illustration of the lead 14. A connector assembly 40 is disposed at or near the proximal region 18 of the lead 14 while a distal assembly 42 is disposed at or near the distal region 20 of the lead 14. Depending on the functional requirements of the CRM system 10 (see FIG. 1) and the therapeutic needs of a patient, the distal region 20 may include one or more electrodes. In the illustrated embodiment, the distal region 20 includes a pair of coil electrodes 44 and 45 that can function as shocking electrodes for providing a defibrillation shock to the heart 16.

In various embodiments, the lead 14 may include only a single coil electrode. In various other embodiments, the lead 14 includes one or more ring electrodes (not shown) along the lead body 22 in lieu of or in addition to the coil electrodes 44, 45. When present, the ring electrodes operate as relatively low voltage pace/sense electrodes. In short, a wide range of electrode combinations may be incorporated into the lead 14 within the scope of the various embodiments of the present invention.

The connector assembly 40 includes a connector 46 and a terminal pin 48. The connector 46 is configured to be coupled to the lead body 22 and is configured to mechanically and electrically couple the lead 14 to a header on pulse generator 12 (see FIG. 1). In various embodiments, the terminal pin 48 extends proximally from the connector 46 and in some embodiments is coupled to a conductor member (not visible in this view) that extends longitudinally through the lead body 22 such that rotating the terminal pin 48 (relative to the lead body 22) causes the conductor member to rotate within the lead body 22. In some embodiments, the terminal pin 48 includes an aperture extending therethrough in order to accommodate a guide wire or an insertion stylet.

The distal assembly 42 includes a housing 50, within which the fixation helix 24 is at least partially disposed. In some embodiments, the housing 50 includes or accommodates a mechanism that enables the fixation helix 24 to move distally and proximally relative to the housing 50. In some embodiments, the housing 50 may accommodate or include structure that limits distal travel of the fixation helix 24 (relative to the housing 50). As noted above, the fixation helix 24 operates as an anchoring means for anchoring the distal region 20 of the lead 14 within the heart 16. In some embodiments, the fixation helix 24 is electrically active, and is also used as a pace/sense electrode. In some embodiments, the fixation helix 24 is made of an electrically conductive material such as Elgiloy, MP35N, nickel, tungsten, tantalum, iridium, platinum, titanium, palladium, stainless steel as well as alloys of any of these materials. In some embodiments, the fixation helix 24 is made of a non-electrically conductive material such as PES (polyethersulfone), polyurethane-based thermoplastics, ceramics, polypropylene and PEEK (polyetheretherketone).

Figure 3A:
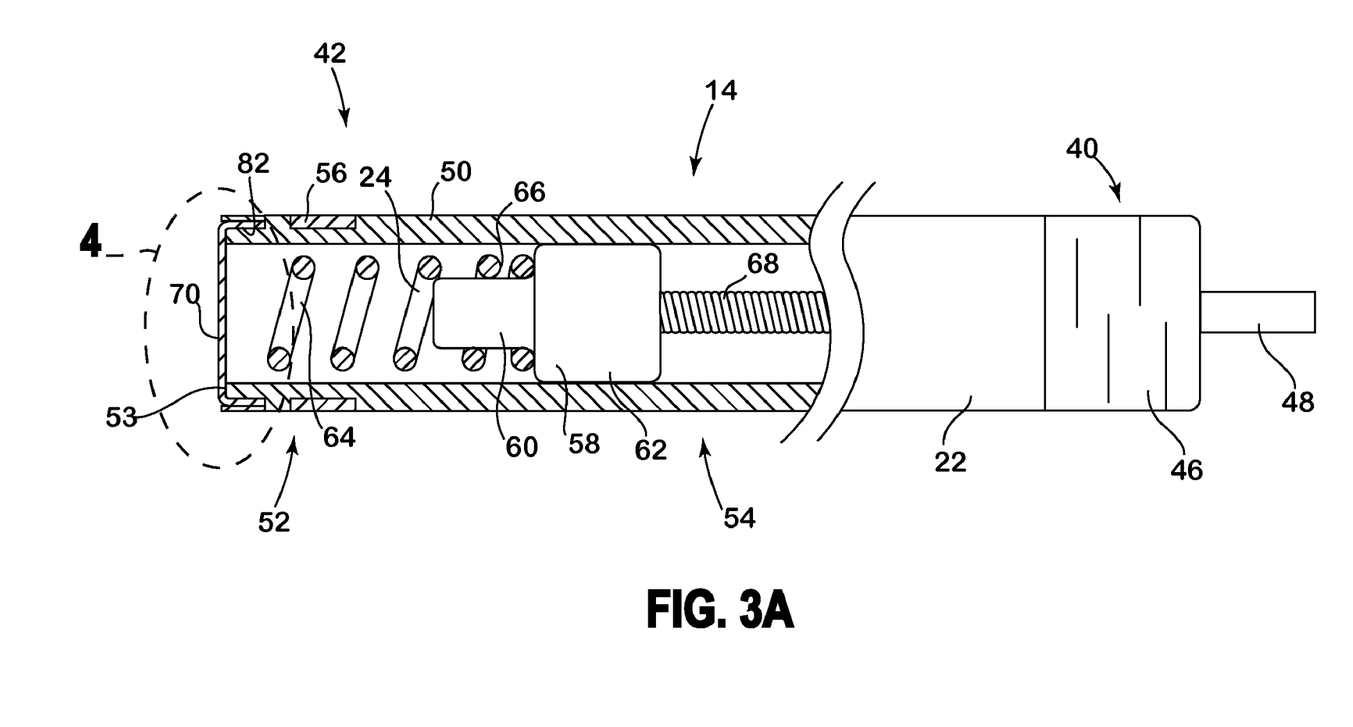
FIG. 3A is a partial cross-sectional view of the lead of FIG. 1, shown in a retracted position.
Figure 3B:
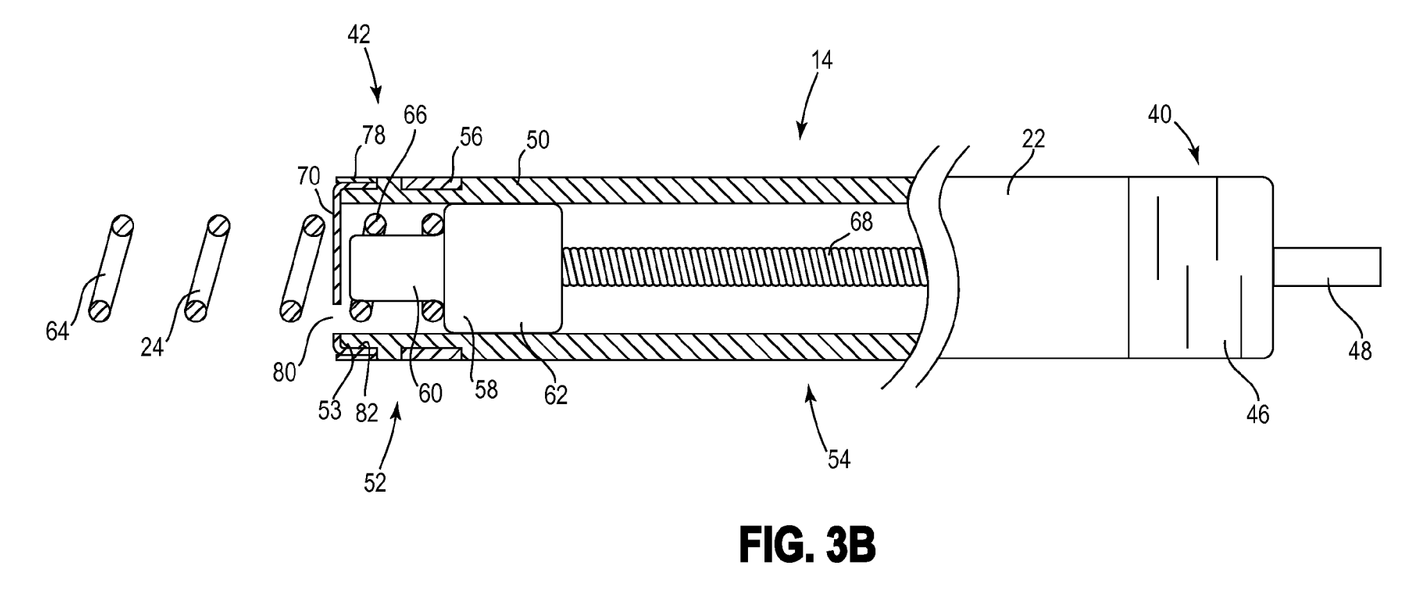
FIG. 3B is a partial cross-sectional view of the lead of FIG. 1, shown in an extended position.
Figure 4:
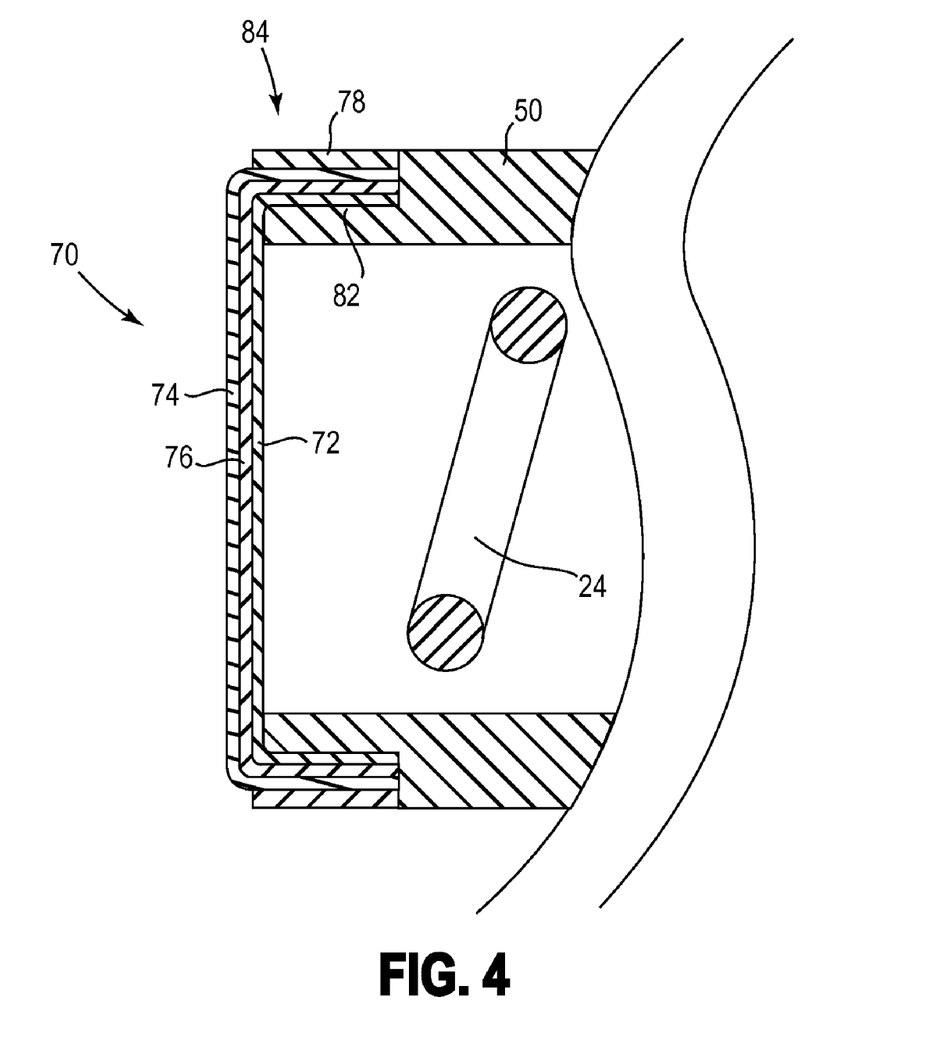
FIG. 4 is an expanded view of a portion of the lead of FIG. 1.

FIGS. 3-4 illustrate an embodiment of a lead including distal assemblies in accordance with the present invention. FIGS. 3A and 3B are partial cross-sections of the lead 14 that include the distal assembly 42 while FIG. 4 provides an enlarged view of a portion of the distal assembly 42. In FIG. 3A, the fixation helix 24 is illustrated in a retracted position while FIG. 3B illustrates the fixation helix 24 in an extended position. In the illustrated embodiment, the fixation helix 24 is electrically active so as to be operable as a pace/sense electrode.

As shown in FIGS. 3A and 3B, the housing 50 includes a distal region 52 and a proximal region 54. The distal region 52 includes a distal end 53. The housing 50 is, in general, relatively rigid or semi-rigid. In some embodiments, the housing 50 is made of an electrically conductive material such as Elgiloy, MP35N, nickel, tungsten, tantalum, iridium, platinum, titanium, palladium, stainless steel as well as alloys of any of these materials. In some embodiments, the housing 50 is made of a non-electrically conductive material such as PES, polyurethane-based thermoplastics, ceramics, polypropylene and PEEK.

In the illustrated embodiment, a drug eluting collar 56 is disposed about an exterior of the housing 50 within the distal region 52. In various embodiments, the drug eluting collar 56 is configured to provide a time-released dosage of a steroid or other anti-inflammatory agent to the tissue to be stimulated, e.g., the heart tissue in which the electrically active fixation helix 24 is implanted. While not illustrated, in some embodiments, the distal assembly 42 may include a radiopaque element disposed under the drug eluting collar 56.

The distal assembly 42 includes a coupler 58 that has a distal portion 60 and a proximal portion 62. In some embodiments, the coupler 58 is formed of a metallic material and is configured to move longitudinally and/or rotationally with respect to the housing 50. In some embodiments, as illustrated, the distal portion 60 may have a relatively smaller diameter (relative to the proximal portion 62) in order to accommodate the fixation helix 24. While not illustrated, in some embodiments the proximal portion 62 is configured to accommodate a seal that provides a seal between the coupler 58 and the housing 50.

The fixation helix 24 has a distal region 64 and a proximal region 66. The proximal region 66 of the fixation helix 24 is secured to the distal portion 60 of the coupler 58. One or more attachment methods are used to secure the fixation helix 24 to the coupler 58. In some embodiments, the proximal region 66 of the fixation helix 24 is welded or soldered onto the distal portion 60 of the coupler 58. In some embodiments, the proximal region 66 of the fixation helix 24 has an inner diameter that is less than an outer diameter of the distal portion 60 of the coupler 58, and thus is held in place via compressive forces. In some embodiments the fixation helix 24 is adhesively secured to the distal portion 60 of the coupler 58. In some embodiments, multiple attachment methods are used.

A conductor member 68 is secured to the proximal portion 62 of the coupler 58, and extends proximally through the lead body 22 to the connector assembly 40. In some embodiments, the conductor member 68 includes or is otherwise formed from a metallic coil. The coupler 58 provides an electrical connection between the conductor member 68 and the fixation helix 24. In the connector assembly 40, the conductor member 68 is coupled to the terminal pin 48 such that rotation of the terminal pin 48 causes the conductor member 68 to rotate. As the conductor member 68 rotates, the coupler 58 and the fixation helix 24 will also rotate. In some embodiments, the fixation helix 24 is rotated via a stylet that is inserted through an aperture that may be formed within the terminal pin 48 (FIG. 2).

The particular arrangement illustrated for facilitating extension and retraction of the fixation helix 24 is exemplary only. In other words, any arrangement, whether now known or later developed, for providing the extendable/retractable functionality of the fixation helix 24 can be utilized in connection with the various embodiments of the present invention. In one embodiment, the lead 14 includes structures such as those described and illustrated in co-pending and commonly assigned U.S. Provisional Patent Application 61/181, 954, the disclosure of which is incorporated by reference herein in its entirety. In other embodiments, a different arrangement for extending and retracting the fixation helix 24 is utilized.

The distal assembly 42 includes a laminate distal seal 70 having several layers. As best seen in FIG. 4, in the illustrated embodiment the laminate distal seal 70 includes an inner layer 72, an outer layer 74 and an intervening elastomeric layer 76. In some embodiments, the inner layer 72 and the outer layer 74 are formed from ePTFE, or expanded polytetrafluoroethylene.

In the illustrated embodiment, the laminate distal seal 70 is stretched or otherwise disposed across the distal end 53 of the housing 50 and is held in place via a fixation ring 78. In some embodiments, the laminate distal seal 70 can be considered as being disposed approximately perpendicular to an axis running longitudinally through the fixation helix 24 and the coupler 58.

The laminate distal seal 70 provides functionality to the lead 14. As discussed, in some embodiments, the outer layer 74 of the laminate distal seal 70 is configured to encourage tissue ingrowth. In some embodiments, the outer layer 74 of the laminate distal seal 70 is configured to discourage tissue ingrowth. In some embodiments, the inner layer 72 of the laminate distal seal 70 is configured to facilitate penetration of the distal seal by the fixation helix 24. It is contemplated that the laminate distal seal 70 may simplify the construction of the distal assembly 42 by reducing or eliminating a need for seals that might otherwise be disposed within the housing 50.

In some embodiments, such as illustrated in FIG. 3A, the laminate distal seal 70 is intact when the fixation helix 24 is in the retracted position, thereby readily sealing the interior of the housing 50 when the lead 14 is being advanced through the patient's vasculature. Once the lead 14 is in place in a desired cardiac location, the fixation helix 24 can be advanced to the extended position in which the fixation helix 24 penetrates into the heart tissue to anchor the lead 14. As the fixation helix 24 moves from the retracted position to the extended position, it will be appreciated that the fixation helix 24 pierces the laminate distal seal 70, thereby forming an aperture 80 therethrough, and then extends distally through the aperture 80. In some embodiments, it is contemplated that the laminate distal seal 70 may include a preformed hole or slot to accommodate the fixation helix 24. In some cases, particularly in a heart failure lead, the laminate distal seal 70 may include a preformed hole that is configured to accommodate a guidewire.

In some embodiments, the elastomeric layer 76 seals around the fixation helix 24 as the fixation helix 24 penetrates the elastomeric layer 76, thereby maintaining a seal around the fixation helix. The elastomeric layer 76 may be formed of materials that provide the elastomeric layer 76 with the ability to prevent tissue ingrowth, provide a fluid barrier, help prevent or limit tearing of the ePTFE layer(s), and the like. An example of a suitable material is silicone. In some embodiments, the material of the elastomeric layer 76 may include one or more fillers or additives for tailoring the physical characteristics, e.g., radiopacity, lubriciousness, stiffness, and the like, of the elastomeric layer 76. Examples of suitable fillers include but are not limited to one or more of barium sulfate, bismuth subcarbonate, titanium dioxide, PTFE (polytetrafluoroethylene) and metallic particles.

In some embodiments, the inner layer 72 is formed of ePTFE having an inter-nodal distance (or average pore size) that is selected to permit the fixation helix 24 to easily penetrate into the laminate distal seal 70. In some embodiments, the outer layer 74 is formed of ePTFE having an average inter-nodal distance in the range of about 5 to about 75 microns and thus is configured to encourage tissue ingrowth. In some embodiments, the outer layer 74 is formed of ePTFE having an average inter-nodal distance that is greater than about 75 microns and thus is configured to discourage tissue ingrowth.

In the illustrated embodiment, the laminate distal seal 70 has a total of three layers. In some embodiments, the laminate distal seal 70 may include other layers. For example, the inner layer 72 and/or the outer layer 74 may be each include multiple layers of ePTFE, or could include layers of other polymers. In some embodiments, the laminate distal seal 70 may include the outer layer 74 of ePTFE but not include the inner layer 72.

In some instances, a layer of ePTFE (expanded polytetrafluoroethylene) can be classified as having a predominant grain direction. When ePTFE, having these characteristics, is penetrated, it will tend to split along the predominant grain direction. In some embodiments, the ePTFE forming the inner layer 72 may have a predominant grain direction extending in a particular direction within the plane of the inner layer 72. Similarly, the ePTFE forming the outer layer 74 may have a predominant grain direction extending in a particular direction within the plane of the outer layer 74.

In some embodiments, the inner layer 72 and the outer layer 74 are arranged such that the predominant grain direction of the inner layer 72 and the predominant grain direction of the outer layer 74 are transverse to one another so as to be oriented in a cross-web fashion. As a result, any tearing or splitting that may occur in one layer is less likely to be propagated in another layer. In some embodiments, the inner layer 72 and the outer layer 74 are formed of biaxially stretched ePTFE. In some embodiments, the ePTFE has nodes that are arranged in a starlike pattern, having a number of fibrils extending between nodes.

The fixation ring 78 is configured to secure the laminate distal seal 70 to the distal region 52 of the housing 50. In some embodiments, as illustrated, the distal region 52 of the housing 50 includes a recessed region 82 that is sized to accommodate the fixation ring 78 as well as a periphery 84 (see FIG. 4) of the laminate distal seal 70 without increasing an overall outer diameter of the distal assembly 42. In some embodiments, the distal region 52 of the housing 50 has a constant outer diameter and thus the fixation ring 78 and the periphery of the laminate distal seal 70 extends above the outer surface of the housing 50.

In some embodiments, the fixation ring 78 is a metal ring and is sized to provide a compressive fit about the distal region 52 (and/or the recessed region 82, if present) of the housing 50 and the periphery 84 of the laminate distal seal 70. In some embodiments, the fixation ring 78 is formed of a metal such as Elgiloy, MP35N, nickel, tungsten, tantalum, iridium, platinum, titanium, palladium, stainless steel, as well as alloys of any of these materials and may be crimped or swagged into position.

In some embodiments, the fixation ring 78 is a polymeric ring and is sized to fit over the distal region 52 of the housing 50 (and/or the recessed region 82, if present) and the periphery 84 of the laminate distal seal 70. The fixation ring 78 is formed of a polymer such as PES (polyethersulfone), polyurethane-based thermoplastics, ceramics, polypropylene and PEEK (polyetheretherketone) and in some embodiments can be at least partially melted to secure the laminate distal seal 70 in place. In some embodiments, the inner layer 72 and/or the outer layer 74, particularly if made of ePTFE, may at least partially melt and thus may contribute to securing the laminate distal seal 70 in place at the distal end 53 of the housing 50.

In some embodiments, the laminate distal seal 70 may instead be secured to the distal region 52 of the housing 50 via the drug collar 56, and in such embodiments the fixation ring 78 may be absent. In other embodiments, the laminate distal seal 70 may be secured to the housing 50 by using adhesives or ultrasonic welding. In some embodiments, the laminate distal seal 70 may be over-molded to the distal region 52 of the housing 50. In some embodiments, the laminate distal seal 70 may be secured to the distal region 52 of the housing 50 via a heat shrink material.

In the illustrated embodiment, the lead 14 is shown as being an extendable/retractable active fixation lead. In some embodiments, the laminate distal seal 70 may be employed with a fixed helix active fixation lead. If used with a fixed helix lead, for example, the laminate distal seal 70 may include the elastomeric layer 76 and the outer layer 74, particularly if the outer layer 74 includes or is made of ePTFE, but may not include the inner layer 72. In some embodiments, if the fixation helix is fixed in position, the inner layer 72 that otherwise provides a starting point for an extendable/retractable fixation helix may be omitted.

Figure 5:
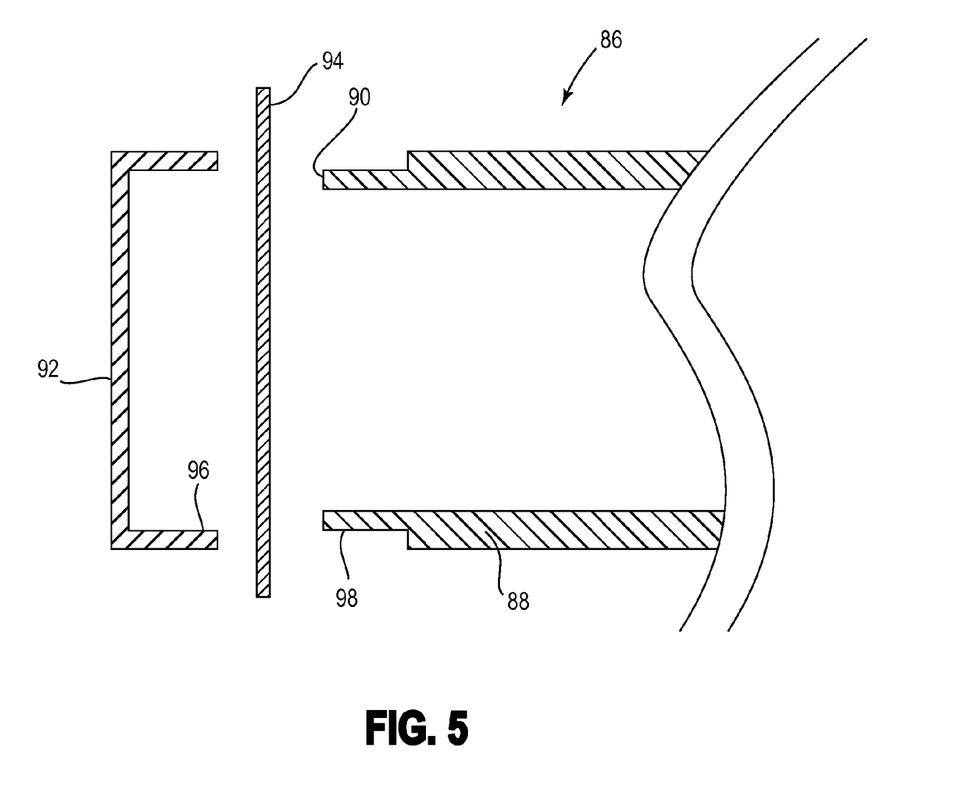
FIG. 5 is an exploded view of a portion of a lead in accordance with an embodiment of the present invention.

FIG. 5 is an exploded view of a distal portion of a lead 86 in accordance with an embodiment of the present invention. In the illustrated embodiment, the lead 86 includes a housing 88 having a distal end 90 and an end cap 92, and is in many respects similar or identical to the lead 14 described above. As shown, the lead 86 includes a laminate distal seal 94 disposed between the distal end 90 of the housing 88 and the end cap 92. It will be appreciated that the end cap 92 may have a variety of different forms, and may include one or more apertures (not shown) to permit the fixation helix 24 to extend through the end cap 92. In some embodiments, as illustrated, the end cap 92 may have a ring shape.

The laminate distal seal 94 may include one or more ePTFE layers and may be configured the substantially the same as or identical to the laminate distal seal 70 discussed previously with respect to FIG. 4. In some embodiments, for example, the laminate distal seal 94 may include an elastomeric layer sandwiched between inner and outer ePTFE layers.

The end cap 92 includes a first attachment surface 96 that cooperates with a corresponding second attachment surface 98 disposed within the housing 88. In some embodiments, the first attachment surface 96 and the second attachment surface 98 may, in combination, provide a threaded attachment between the housing 88 and the end cap 92. In other embodiments, the first attachment surface 96 and the second attachment surface 98 may, in combination, provide a snap-fit between the housing 88 and the end cap 92. In other embodiments, the end cap 92 may be welded or adhesively secured onto the housing 88. When the end cap 92 is attached to the housing 88, the laminate distal seal 94 will be captured between the end cap 92 and the housing 88 and thus will be secured in place. In some embodiments, any portion of the laminate distal seal 94 extending radially beyond its captured portion may be trimmed off.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An implantable lead comprising:
    a flexible body extending between a proximal end and a distal end;
    a connector assembly secured to the proximal end for coupling the lead to an implantable medical device, the connector assembly including a terminal pin rotatable relative to the body;
    a conductor member disposed longitudinally within the body and coupled to the terminal pin, the conductor member rotatable relative to the body; and
    a distal assembly coupled to the distal end of the body and including:
        a housing having a distal region and a proximal region, the proximal region fixedly coupled to the distal end of the body, the distal region including a distal end;
        a coupler rotatably disposed within the housing, the coupler having a proximal end and a distal end, the proximal end connected to the conductor member;
        a helical electrode fixedly secured to the coupler; and
        a laminate distal seal disposed across the distal end of the housing and at least substantially sealing an interior of the housing, the laminate distal seal including an inner ePTFE layer, an outer ePTFE layer and an intervening elastomeric layer, the inner ePTFE layer and the outer ePTFE layer each having a predominant grain direction, the inner ePTFE layer and the outer ePTFE layer disposed so that the predominant grain direction of each of the two layers are offset from each other;
    wherein the terminal pin is rotatably engaged with the coupler via the conductor member such that rotation of the terminal pin causes the coupler and the helical electrode to rotate and therefore translate relative to the housing.

2. The implantable lead of claim 1, wherein the helical electrode pierces the laminate distal seal as the helical electrode translates distally.

3. The implantable lead of claim 1, wherein the elastomeric layer comprises silicone.

4. The implantable lead of claim 1, wherein the inner ePTFE layer is configured to be easily penetrated by the helical electrode to help guide the helical electrode into the laminate distal seal.

5. The implantable lead of claim 1, wherein the outer ePTFE layer is configured to inhibit tissue ingrowth.

6. The implantable lead of claim 1, wherein the outer ePTFE layer is configured to encourage tissue ingrowth.

* * * * *